US012746143B2

(12) United States Patent
White et al.

(10) Patent No.: US 12,746,143 B2
(45) Date of Patent: Sep. 29, 2026

(54) ADJUSTABLE NAIL BED SPLINT

(71) Applicant: Wichita State University, Wichita, KS (US)

(72) Inventors: Joel White, Wichita, KS (US); Stephen Granberry, Wichita, KS (US)

(73) Assignee: WICHITA STATE UNIVERSITY, Wichita, KS (US)

( * ) Notice: Subject to any disclaimer, the term of this patent is extended or adjusted under 35 U.S.C. 154(b) by 681 days.

(21) Appl. No.: 18/152,532

(22) Filed: Jan. 10, 2023

(65) Prior Publication Data

US 2023/0218421 A1 Jul. 13, 2023

Related U.S. Application Data

(60) Provisional application No. 63/301,075, filed on Jan. 20, 2022, provisional application No. 63/298,035, filed on Jan. 10, 2022.

(51) Int. Cl.
*A61F 5/11* (2006.01)

(52) U.S. Cl.
CPC .................................... *A61F 5/11* (2013.01)

(58) Field of Classification Search
CPC .......... A61F 13/064; A61F 2013/00404; A61F 5/019; A61F 13/063; A61F 5/11; A61F 5/0111; A61F 5/0116; A61F 5/0585; A61F 13/06; A43B 3/102; A43B 5/12; A43B 7/1445; A43B 7/1425; A43B 7/1435

See application file for complete search history.

(56) References Cited

U.S. PATENT DOCUMENTS 4,819,623 A * 4/1989 Ogunro ................. A61F 13/105 602/22
8,210,185 B2 * 7/2012 Fracassi ................. A45D 31/00 132/73

FOREIGN PATENT DOCUMENTS

| | | | | |
|---|---|---|---|---|
| CN | 101031218 B * | 12/2010 | ............. | A45D 31/00 |
| KR | 1164554 B1 * | 7/2012 | ............. | A45D 31/00 |
| KR | 20160099124 A1 * | 2/2015 | ............. | A45D 31/00 |

* cited by examiner

*Primary Examiner* — Ophelia A Hawthorne
(74) *Attorney, Agent, or Firm* — Stinson LLP

(57) ABSTRACT

An adjustable nail bed splint can be fitted to a plurality of patient-specific nail beds of varying shapes. The adjustable nail bed splint includes a splint plate having a proximal end portion and a distal end portion spaced apart along a longitudinal axis and first and second longitudinal edge margins spaced apart along a lateral axis. The splint plate is adjustable for fitment to a patient-specific nail bed. The splint plate is stiffer along the longitudinal axis than along the lateral axis to facilitate deforming the splint plate laterally to generally conform to a lateral curvature of the patient-specific nail bed. A kit for splinting nail beds includes an adjustable nail bed splint within sterile packaging. The adjustable nail bed splint is configured to be fitted to a plurality of patient-specific nail beds of varying shapes.

20 Claims, 13 Drawing Sheets

PIOR ART

ADJUSTABLE NAIL BED SPLINT

CROSS-REFERENCE TO RELATED APPLICATION

This application claims the benefit of U.S. Patent Application No. 63/298,035, filed Jan. 10, 2022, and U.S. Patent Application No. 63/301,075, filed Jan. 20, 2022, the entire contents of which are incorporated by reference in their entirety for all purposes.

FIELD

The present disclosure generally relates to orthopedic splints, and more specifically, to nail bed splints to minimize tissue scarring and promote nail plate regrowth.

BACKGROUND

Nail bed splints are used by medical professionals to treat a finger or toe injury after loss or removal of the patient's nail bed plate. A nail bed splint is used to minimize scarring and provide protection of tissue underneath and around the nail so that proper healing can occur post-injury. Without the patient's original nail plate, the tissue underneath the nail known as a nail bed and the surrounding tissue known as a nail fold are more susceptible to further injury. Common injuries include a subungual hematoma, a nail bed laceration, or a nail bed avulsion. Further, without the nail plate, the tissue is more susceptible to scarring during healing of the tissue, resulting in deformity of a new nail plate. Previous nail bed splints, such as the one found in U.S. Pat. No. 4,819,623, are configured to foster cosmetically pleasing healing of nail bed tissue, as best shown in FIG. 1. The nail bed splint of U.S. Pat. No. 4,819,623 is surgically secured into an eponychium region of a patient's finger through sutures and maintains contact with the nail bed, which successfully fosters cosmetically pleasing healing of nail bed tissue once secured onto the finger of the patient. The nail bed splint of U.S. Pat. No. 4,819,623 is manufactured to have a fixed curvature and shape.

BRIEF SUMMARY

In one embodiment, the present disclosure provides an adjustable nail bed splint that is configured to be fitted to any of a plurality of patient-specific nail beds of varying shapes and sizes. The adjustable nail bed splint includes a splint plate having a proximal end portion and a distal end portion spaced apart along a longitudinal axis and first and second longitudinal edge margins spaced apart along a lateral axis perpendicular to the longitudinal axis. The splint plate is configured to be adjusted for fitment to a patient-specific nail bed. The splint plate is stiffer along the longitudinal axis than along the lateral axis to facilitate deforming the splint plate laterally to generally conform to a lateral curvature of the patient-specific nail bed.

The present disclosure also provides a kit for splinting nail beds. The kit for splinting nails includes sterile packaging and an adjustable nail bed splint removably received in the sterile packaging. The adjustable nail bed splint is configured to be fitted to any of a plurality of patient-specific nail beds of varying shapes.

The present disclosure also provides an adjustable nail bed splint being configured to be fitted to any of a plurality of patient-specific nail beds of varying shapes. The adjustable nail bed splint including a splint plate having a proximal end portion and a distal end portion spaced apart along a longitudinal axis and first and second longitudinal edge margins spaced apart along a lateral axis perpendicular to the longitudinal axis. The splint plate includes a plurality of longitudinal cut guides extending parallel to the longitudinal axis at spaced apart locations along the lateral axis. Each of the longitudinal cut guides is configured to guide cutting of the splint plate along a respective longitudinal cut line to adjust a width of the splint plate along the lateral axis.

Other aspects and features will be apparent hereinafter.

BRIEF DESCRIPTION OF DRAWINGS

For a better understanding of the nature and objects of the disclosure, reference should be made to the following detailed description taken in conjunction with the accompanying drawings, in which:

FIG. 5A is an enlarged view of a portion of FIG. 5.

Figure 1:
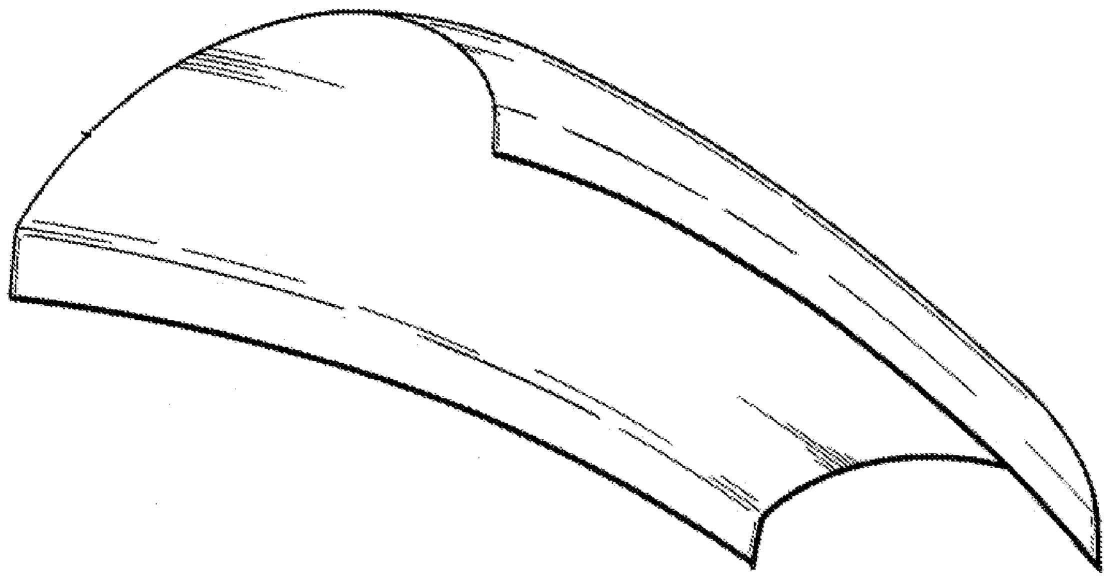
FIG. 1 is illustration of a nail bed splint of U.S. Pat. No. 4,819,623.

Reference is made in the following detailed description of preferred embodiments to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim.

DETAILED DESCRIPTION

Referring now to the drawings, an exemplary embodiment of an adjustable nail bed splint of this disclosure is generally indicated at reference number 10. The adjustable nail bed splint 10 is used when an injury to a patient's nail bed requires a temporary splint so that a patient's nail may regrow with minimal deformity. The adjustable nail bed splint 10 comprises a splint plate 12 including a proximal end portion 14 and a distal end portion 16 spaced apart along a longitudinal axis 18 and first and second longitudinal edge margins 20, 22 spaced apart along a lateral axis 24 that is perpendicular to the longitudinal axis. The splint plate 12 can be reconfigured from its initial size and shape to fit a wide variety of different patient specific nail beds. More particularly, the splint plate 12 is configured to be cut to shape and selectively deformed such that the splint plate generally conforms to a lateral curvature of a patient-specific nail bed B. The inventors have recognized that the nail bed splint of U.S. Pat. No. 4,819,623 is limited by its fixed size and shape. The nail bed splint disclosed therein can only be used on certain fingers of certain patients. In order to facilitate wider use of the nail bed splint of U.S. Pat. No. 4,819,623, a medical establishment must maintain an inventory of splints of different sizes. Even then, the splints of a select number of fixed sizes and shapes may not always fit every patient properly. In comparison with these existing nail bed splints, the inventors believe that the illustrated adjustable nail bed splint 10 provides substantial improvements in fitment and in accommodating a wide range of finger and toe sizes and shapes.

In an exemplary embodiment, the splint plate 12 is formed from one monolithic and unitary piece of material. Suitable materials chosen for the splint plate 12 are preferably inert to bodily fluids and do not elicit an immune or sensitization response from the patient's body when in contact with a patient's tissues. Suitable materials for the splint plate 12 are, in other words, biocompatible materials. In an exemplary embodiment, the suitable material is polyethylene terephthalate sold by FlexCon of Spencer, Massachusetts under the name "FLX002252." In addition to being biocompatible, in an exemplary embodiment, materials suitable for the splint plate 12 are also capable of being embossed. Embossing of the splint plate allows for incorporation of additional design features, including cutting guides and corrugations, allowing for directional device properties. The splint plate 12, in one or more embodiments, is formed from material that is capable of plastic deformation (e.g., bending) such that splint plate 12 can be bent to conform to a nail bed and then hold its bent shape.

Figure 2:
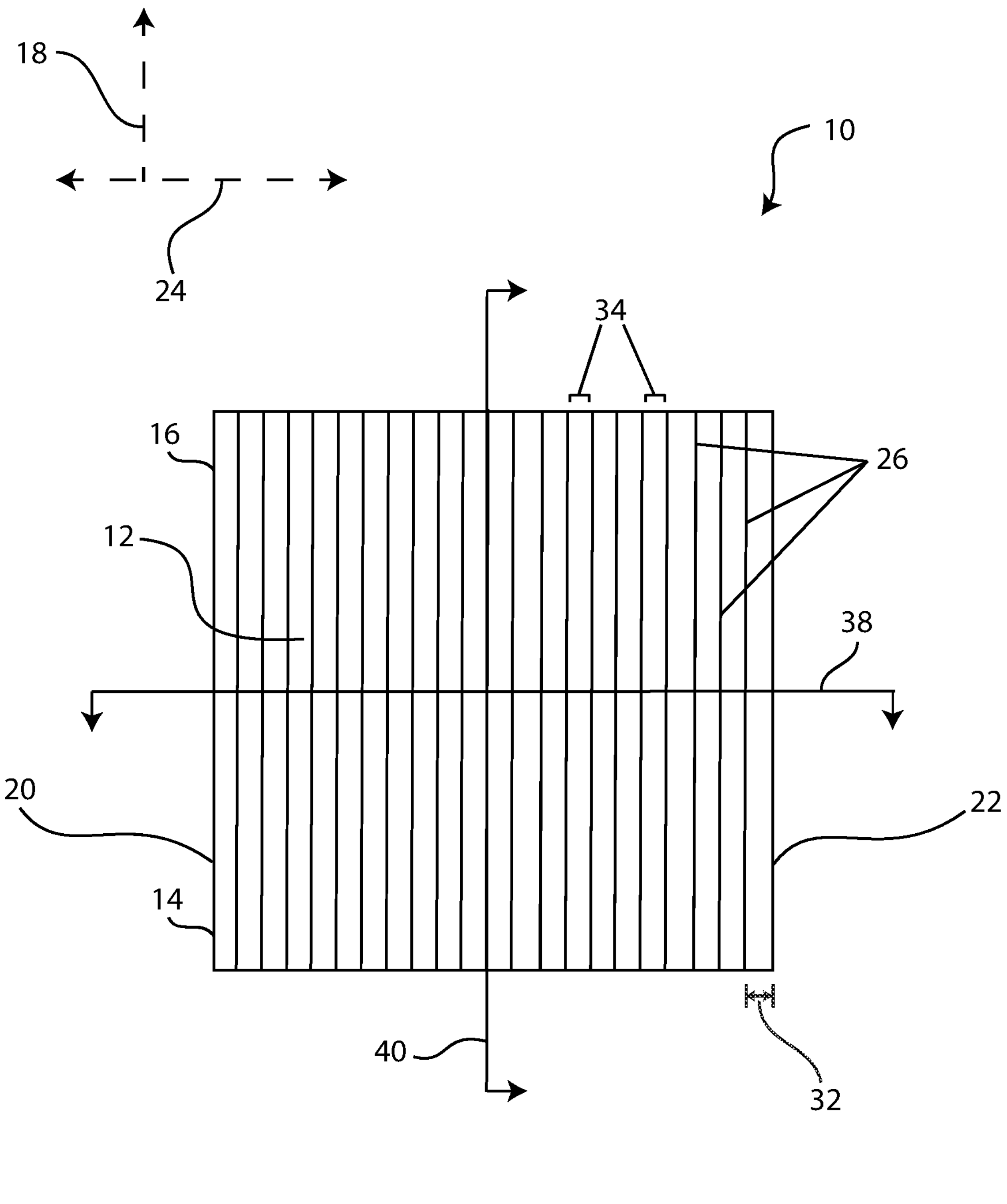
FIG. 2 is a top plan view of an adjustable nail bed splint in accordance with the present disclosure.
Figure 13:
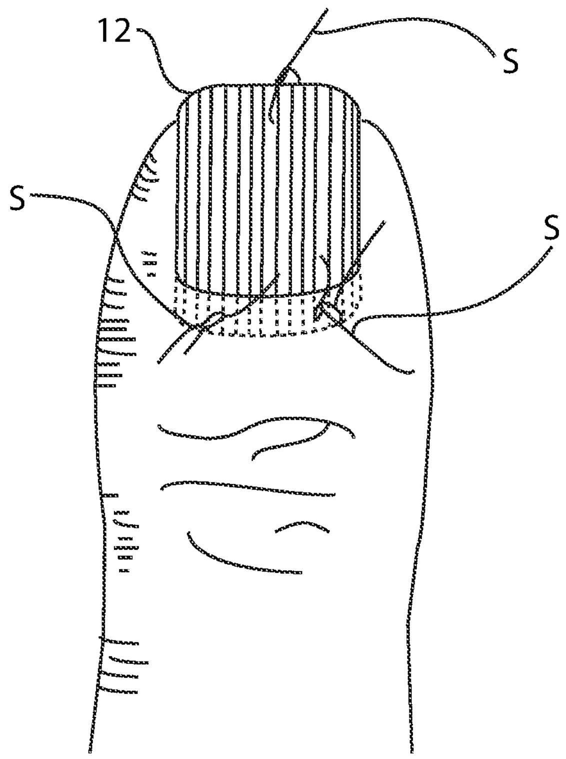
FIG. 13 is a top view of the nail stent of FIG. 10 showing a portion of the nail bed splint that is seated under the eponychial fold F.

In the illustrated embodiment, the splint plate 12 is intended for use in forming a single nail bed splint 10. Referring to FIG. 2, the illustrated splint plate 12 comprises a rectangular (e.g., square) sheet of plastically deformable material having a bottom contact side 28 and an opposite top side 30. Referring to FIG. 13, the single-use splint plate 12 is preferably provided as part a splinting kit 48 in sterile packaging 50. The splint plate 12 is generally oversized in relation to a typical patient-specific nail bed. The splint plate 12 has a length along the longitudinal axis 18 and a width along the lateral axis 24. In one or more embodiments, the length is in an inclusive range of from ½" to 1.25" and/or the width is in an inclusive range of from ¼" to 1.25". As explained more fully below, the splint plate 12 may be configured for being cut to a size and shape that matches a patient-specific nail bed. Alternatively, instead of providing individual oversized splint plates for each nail bed, the nail bed splints may be cut onsite from rolls of splint material sized for forming a plurality of nail bed splints.

Figure 3:
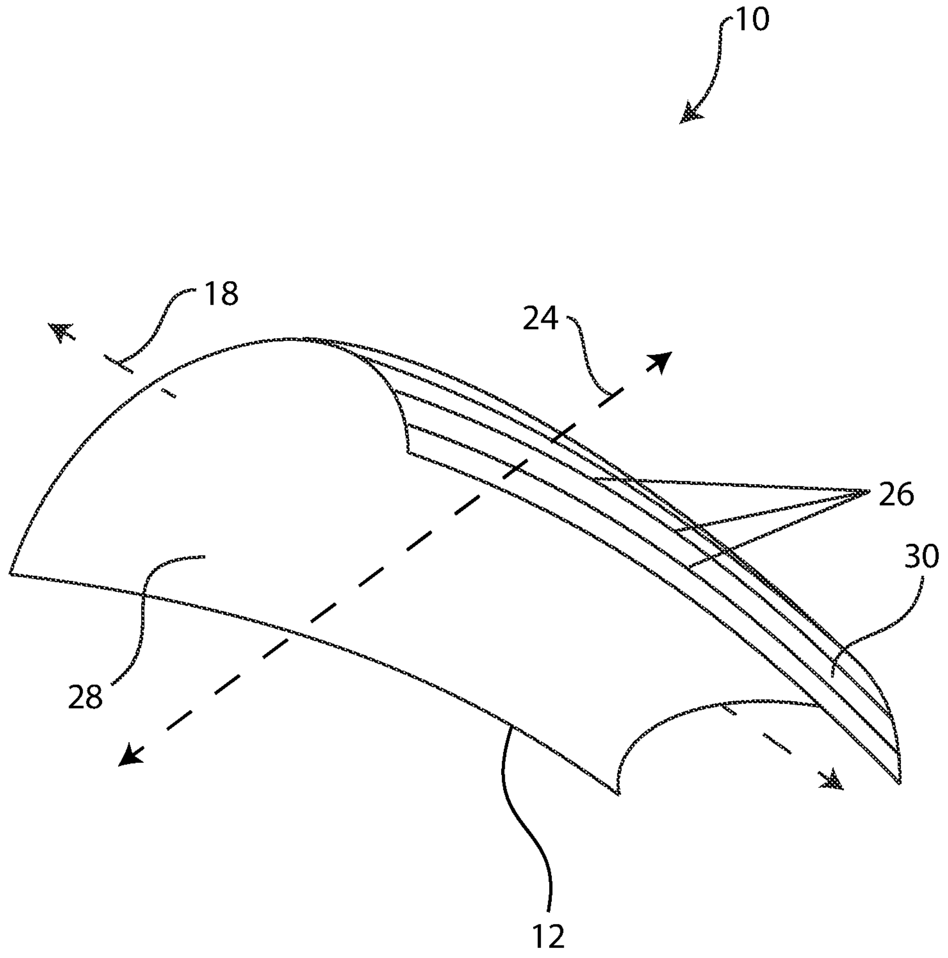
FIG. 3 is a perspective of the adjustable nail bed splint including a prefabricated curve.

In one or more embodiments, the splint plate 12 is provided as a flat sheet of material that is deformed by the end user to have a lateral curvature corresponding to the curvature of the patient-specific nail bed. In another embodiment, the splint plate 12 can be manufactured and provided in sterile packaging 50 with an initial lateral curvature, as shown in FIG. 3. In the case of the splint plate 12 being produced with the initial lateral curvature, the splint plate will be deformable to another lateral curvature different than the initial lateral curvature. For example, the radius of curvature of the initial lateral curvature may be greater than the radius of curvature of the subsequent lateral curvature.

Regardless of initial shape, the splint plate 12 is broadly configured to be deformed to a lateral curvature that substantially conforms to the curvature of any patient-specific nail bed. To facilitate adjusting lateral curvature, the illustrated splint plate 12 is formed to have a plurality of longitudinal bending lines 26 at spaced apart locations along the lateral axis. In general, the splint plate 12 is configured to bend with less resistance along the longitudinal bending lines 26 than along longitudinal lines located between the longitudinal bending lines or any line transverse to the longitudinal bending lines. In other words, the splint plate 12 is stiffer along the longitudinal axis 18 than along the lateral axis 24 to facilitate deforming the splint plate laterally. The splint plate 12 has a central longitudinal cross-sectional plane 40 parallel to the longitudinal axis 18 and a central lateral cross-sectional plane 38 perpendicular to the longitudinal axis 18. The splint plate has a longitudinal stiffness corresponding to deformability of the splint plate in the central longitudinal cross-sectional plane 40 and a lateral stiffness corresponding to deformability of the splint plate in the central lateral cross-sectional plane 38. The longitudinal stiffness is greater than the lateral stiffness.

Figure 5:
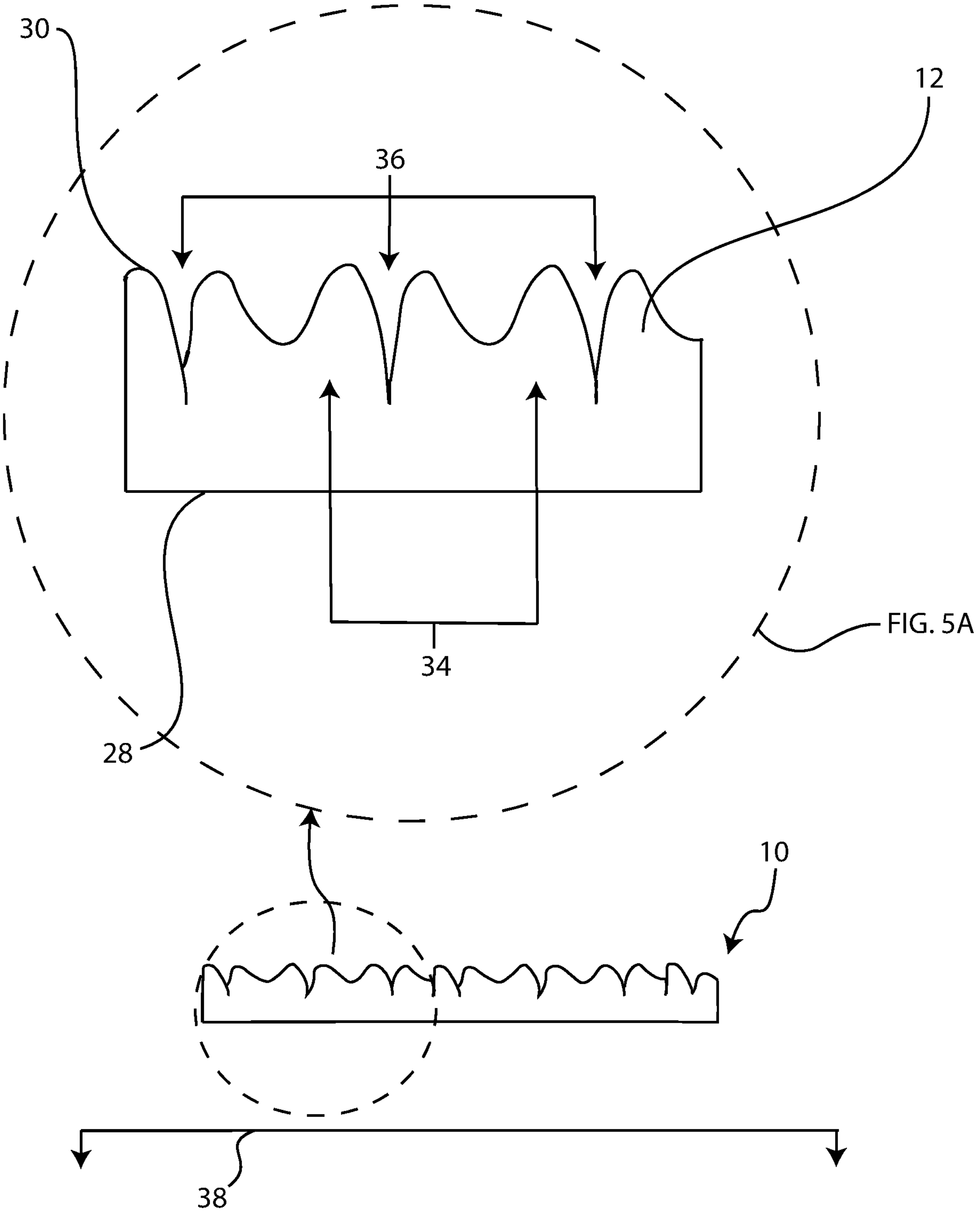
FIG. 5 is a cross-section of the adjustable nail bed splint taken in a lateral plane.

Referring to FIGS. 2 & 5, the longitudinal bending lines 26 are spaced apart along the lateral axis 24 by a lateral spacing distance 32. In the preferred embodiment, the lateral spacing distance 32 is in a range of from 0.5 mm to 2 mm. Between the plurality of parallel longitudinal bending lines 26 are longitudinal segments 34. The longitudinal segments 34 correspond in width to the lateral spacing distance 32 and act as reinforcing ribs. More broadly, the longitudinal segments 34 act as longitudinal reinforcement, such that the splint plate 12 is stiffer along the longitudinal axis 18 than along the lateral axis 24. This reinforces the splint plate against bending the splint plate in any longitudinal plane to aid in protection of the nail bed as well as aid in insertion of the nail splint underneath the eponychial fold F during the splinting procedure.

The longitudinal bending lines 26 can be formed various ways without departing from the scope of the disclosure. For example, by comparison, the splint plate 12 can differ in at least one of thickness, density, and composition along the longitudinal bending lines 26 as compared with along the longitudinal segments 34 between the longitudinal bending lines. In the illustrated embodiment, the splint plate 12 differs in thickness along the longitudinal bending lines 26 versus along the segments 34 between the longitudinal bending lines. For example, in one or more embodiments the splint plate 12 comprises a first thickness T1 along the longitudinal bending lines 26 and a second thickness T2 along the segments 34, wherein T2>T1. In one or more embodiments, the thickness T1 is in an inclusive range of from 3 mils to 7 mils and the thickness T2 is in a range of from 9 mils to 11 mils. In certain embodiments, the reduced-thickness longitudinal bending lines 26 are formed by embossing the top side 30 of the splint plate 12. The illustrated embossments 36 form continuous grooves along the top side 30 of the splint plate. In another embodiment, the longitudinal bending lines 26 can comprise grooves formed along the top side 30 of the splint plate 12 by removing material, instead of embossing. The grooves (whether formed by embossing or material removal) can also be discontinuous without departing from the scope of the disclosure. It is also contemplated that the longitudinal bending lines 26 could be formed by a line of perforations that extend through the entire thickness of the splint plate 12 in one or more embodiments. Further embodiments may form the longitudinal bending lines 26 by varying the composition of the splint plate material at the bending lines. For example, splint plate 12 could be formed in a co-extrusion process that imparts less rigid material at and along the longitudinal bending lines 26.

The use of grooves, whether embossed or formed by removal of material from the top side 30 of the splint plate, is thought to have several advantages in addition to enhanced bending in a lateral plane. For example, the grooved top side 30 of the plate 12 provides enhanced traction for gripping the splint plate during shaping and placement. In addition, the grooves 36 form integral cut lines that help guide a cutting implement when cutting the splint 10 to width.

The bottom contact side 28 of the illustrated splint plate is not embossed and is therefore smooth. When the nail bed splint 10 is placed on a patient's nail bed, the bottom contact side 28 will be in contact with the top surface of the patient's nail bed, providing smooth, continuous contact between the splint and nail bed.

Figure 4:
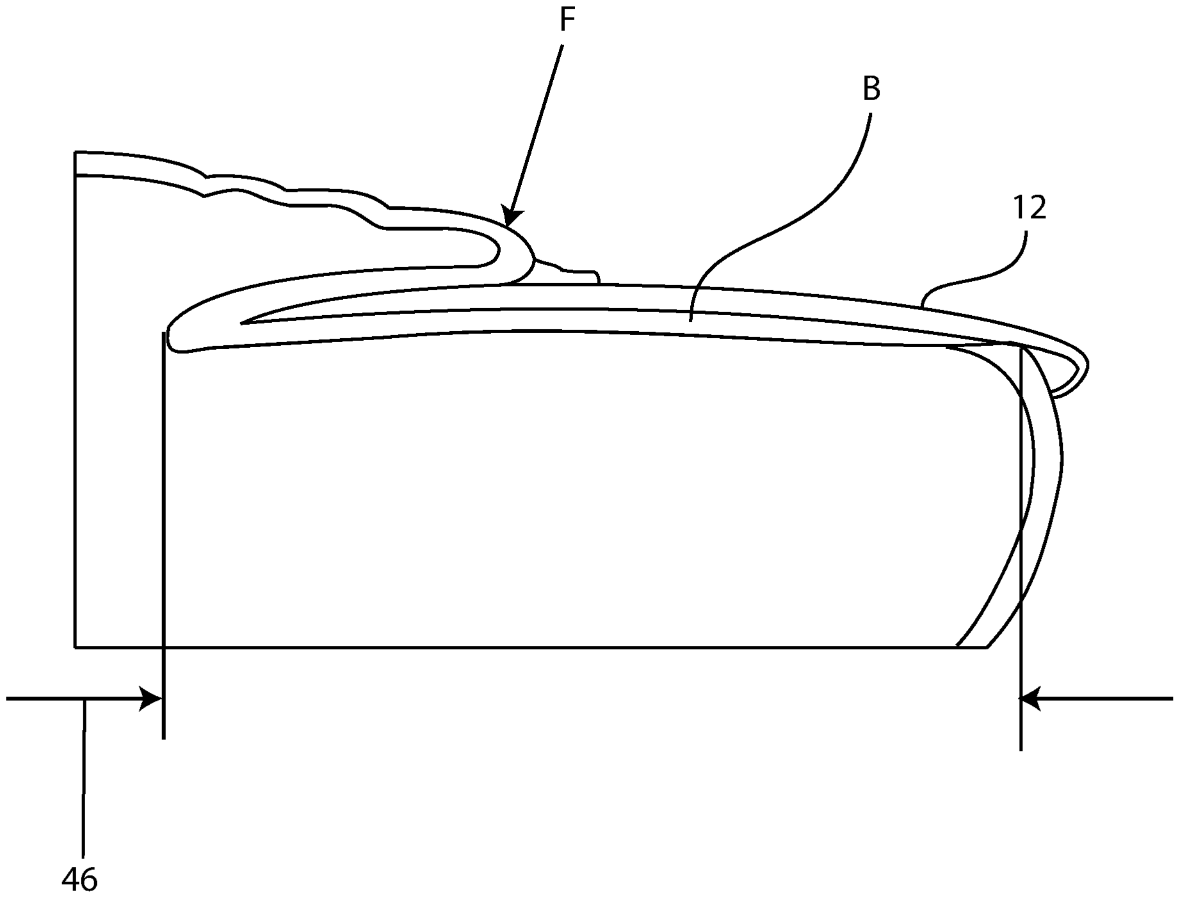
FIG. 4 is a longitudinal cross-sectional illustration of a patient-specific nail bed B.
Figure 6:
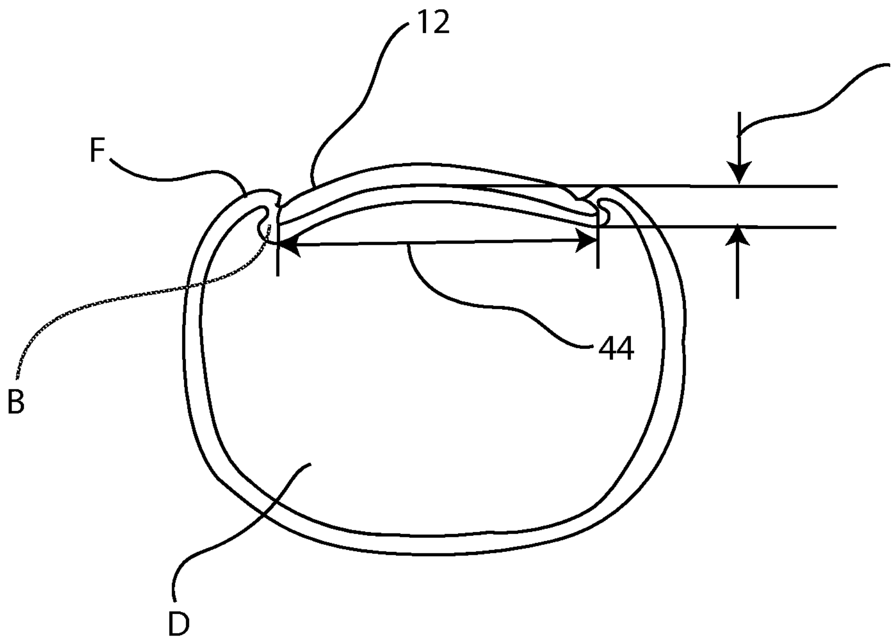
FIG. 6 is an end view of the patient-specific nail bed.

FIGS. 4 and 6 show a typical nail bed B. The nail bed B has a length 46 extending from the base of an eponychial fold F to the fingertip and a width 44 extending perpendicular to the length between the sides of the nail bend. As shown in FIG. 6, the nail bed B is convexly curved along the width 44. The nail bed B has a low point at one or both side edges of the nail bed and a high point at an apex of curvature roughly centered laterally between the side edges. The nail bed B has a height 42 extending vertically from the low point to the high point. The illustrated splint plate 12 is reconfigurable to fit almost any patient-specific nail bed of any realistic nail bed length 46, nail bed width 44, and nail bed height 42. In one or more embodiments, the splint plate 12 can be adjusted to fit a nail bed B having a nail bed length 46 up to 1.25". In certain embodiments, the splint plate 12 can be adjusted to fit a nail bend B having a nail bed width 44 up to 1.25". In an exemplary embodiment, the splint plate 12 can be adjusted to fit a nail bed B having a varied nail bed height 42. The splint plate 12 can be adjusted to form a nail bed splint 10 having a substantially constant radius of curvature or a compound radius of curvature.

As explained above, a single-use splint plate 12 can be provided as a kit 48 in sterile packaging 50. It will be appreciated that the splint plate 12 is not a section removed from the packaging foil but rather a separate article sealed inside the packaging 50. Additional articles useful for nail bed splinting may also be included inside the packaging 50. For example, in one or more embodiments, sutures for securing the nail bed splint 10 to a patient nail bed B are provided inside the packaging with the splint plate 12.

Figure 7:
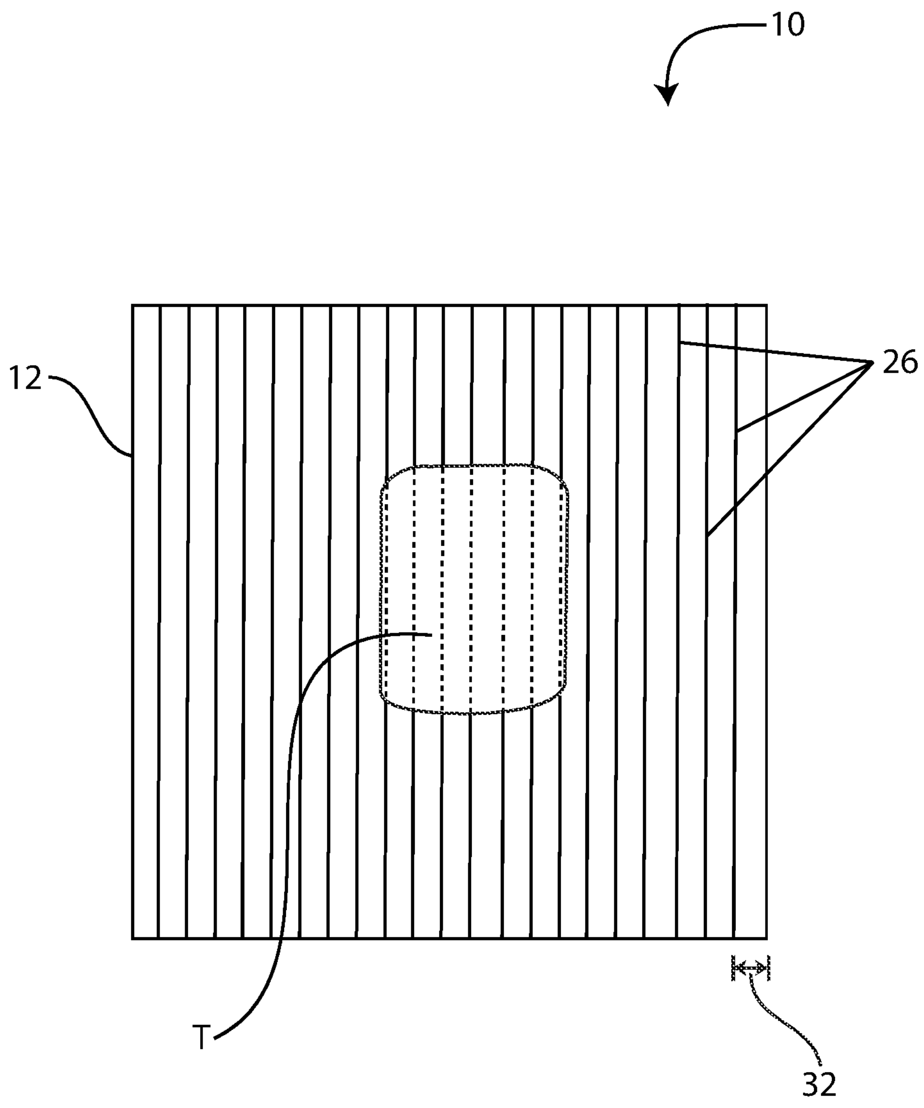
FIG. 7 is an illustration of a trace of the patient-specific nail bed on the splint plate.
Figure 8:
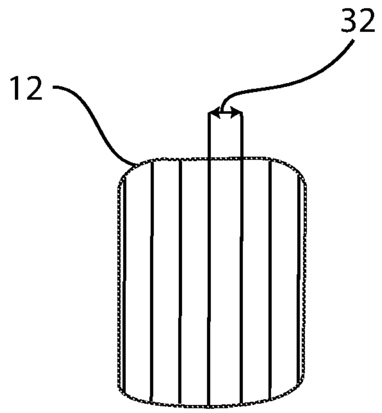
FIG. 8 is an illustration of the nail bed splint after being sized to the patient's specific nail bed.
Figure 9:
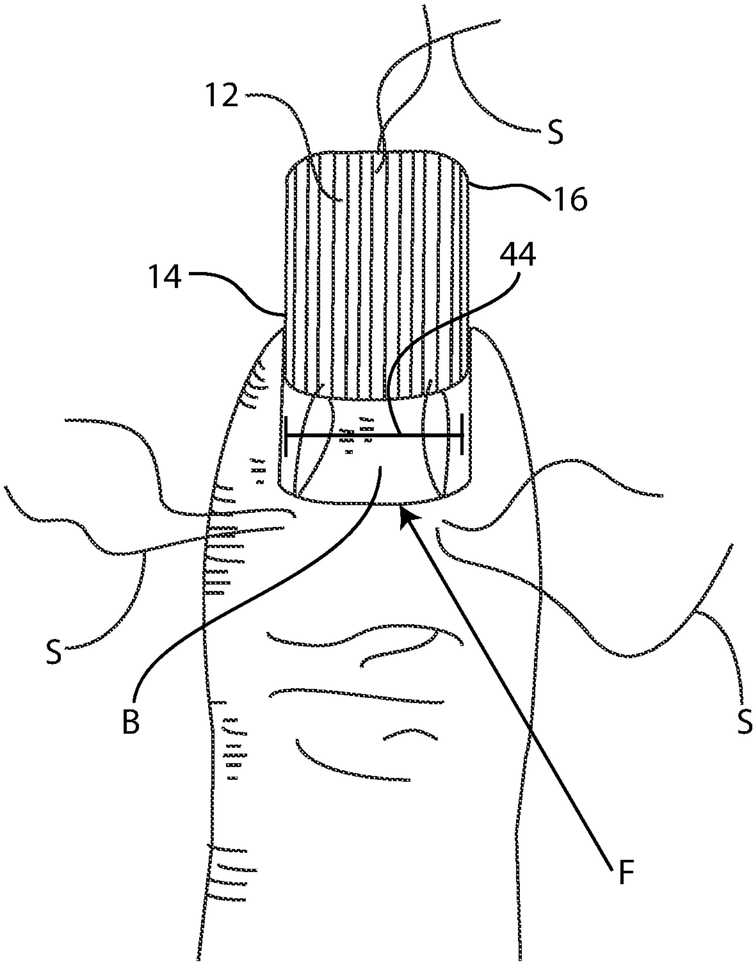
FIG. 9 is a patient-specific nail bed onto which the adjustable splint is partially attached.
Figure 10:
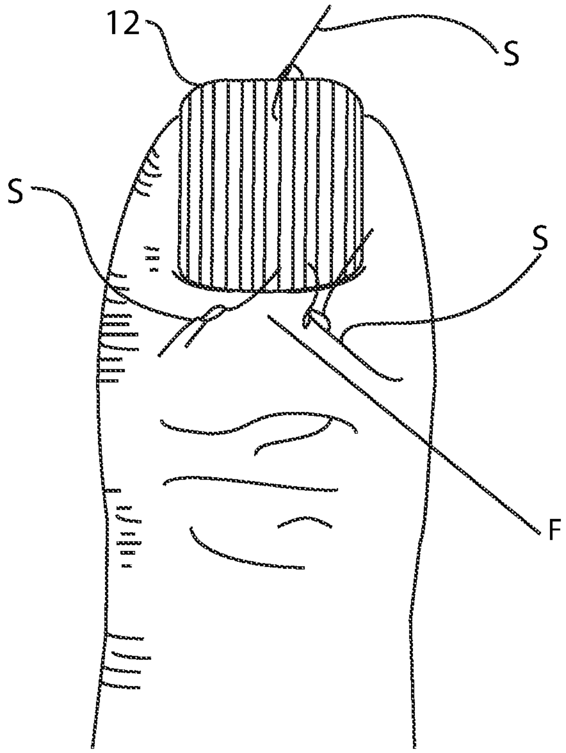
FIG. 10 is a top view of the nail bed splint secured to a patient's finger.
Figure 11:
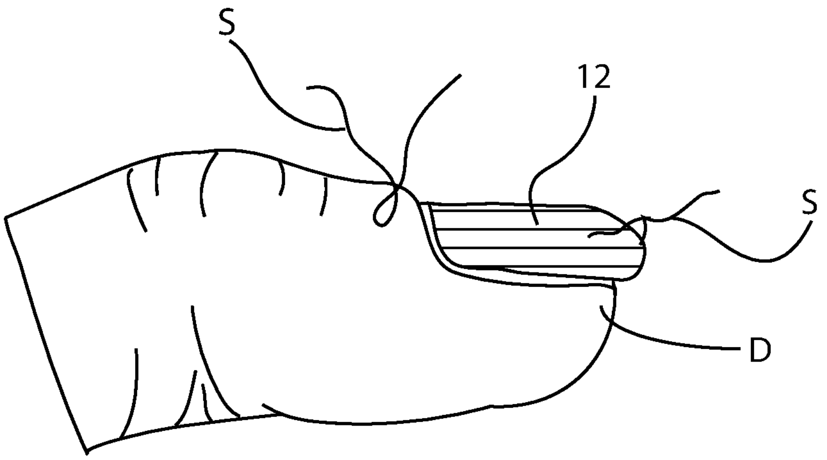
FIG. 11 is a side view of the nail bed splint secured to a patient's finger.
Figure 12:
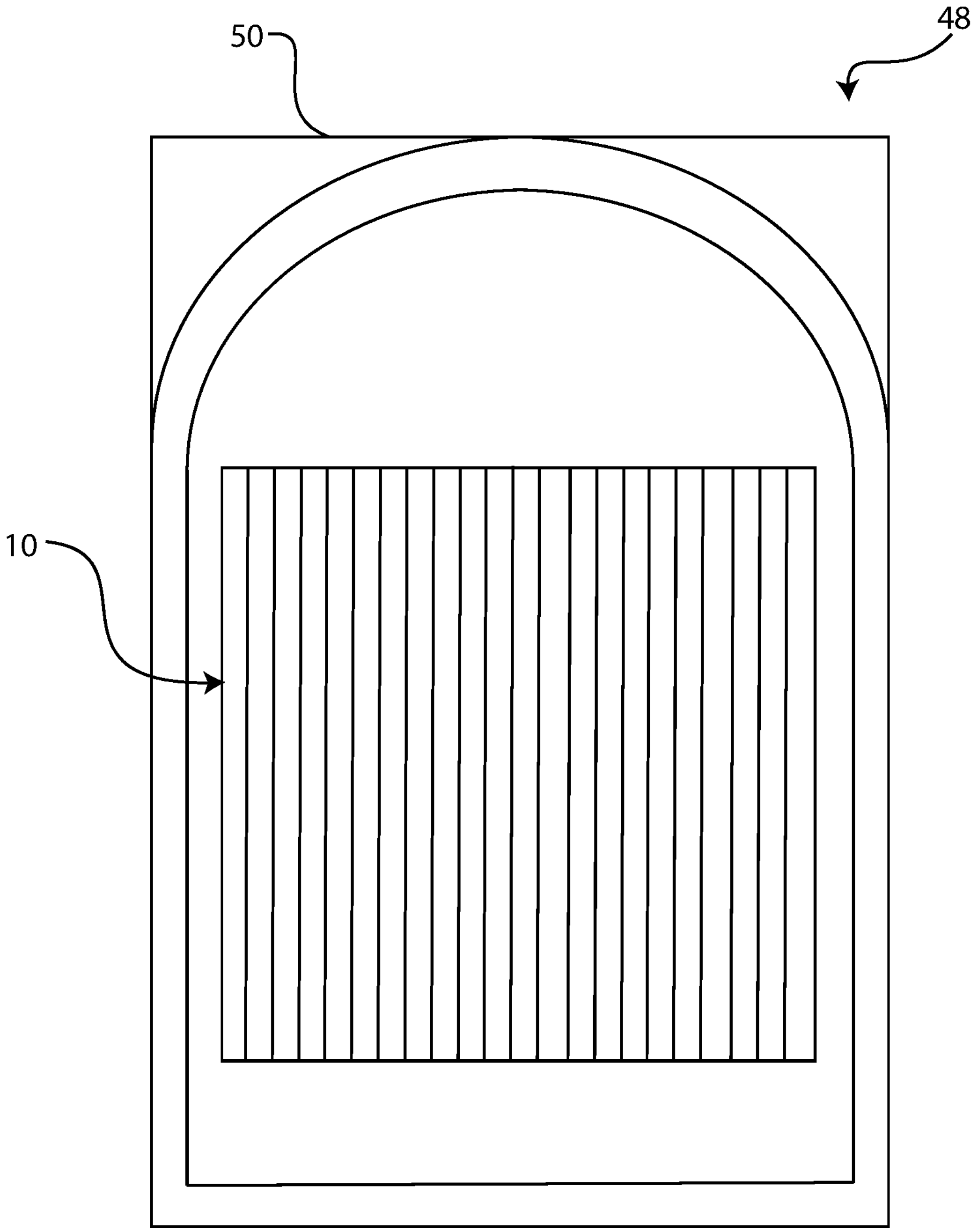
FIG. 12 is a plan view of a kit including the adjustable nail bed splint and sterile packaging.

An exemplary method of using the kit 48 and splint plate 12 to splint a patient nail bed will now be briefly described. Initially, the practitioner removes the splint plate 12 from the packaging 50. Next the practitioner adjusts the splint plate 12 to correspond to the patient-specific nail bed B. To illustrate how the adjustable nail bed splint 10 may be adjusted for fitment to a patient-specific nail bed B, FIG. 7 depicts an initial step of marking a trace T of a patient's nail bed B onto the splint plate 12. The trace T indicates the length 46 and width 44 of the nail bed B, accounting for the nail bed curvature. The practitioner then cuts the splint plate 12 along the trace to form the un-shaped body of the nail bed splint 10. At this point, the surgeon may estimate the lateral curvature of the patient's nail bed and bend the splint 10 along the longitudinal bending lines 26 to approximate the lateral curvature of the patient-specific nail bed B. Once the surgeon has adjusted the splint plate 12 for fitment to the patient's the nail bed B, the splint plate 12 is loosely secured to the patient's nail bed B, with sutures S, as depicted in FIG. 9. The surgeon may make additional adjustments to the splint 10 as needed for better fit. For instance, after partially securing the splint 10 to the patient's nail bed B, the surgeon may need to trim the length or width of the splint plate and/or make further adjustments to the curvature. Once the desired shape is achieved, the sutures S are pulled tight to fully insert the splint plate under the patient's eponychial fold F and then tied, as depicted in FIG. 10. While the locations of the sutures S may vary, preferably, the sutures S are placed to limit both upward, and horizontal movement away from the nail bed B. For example, as shown in FIG. 11, the distal end portion 16 of the splint plate 12 is secured to the distal tip D of the patient's finger, while the proximal end portion 14 is secured to the eponychial fold F via sutures S.

As known to one skilled in the art, a typical eponychial fold extends 0.2 inches over the nail bed, and the splint plate 12 should sit fully nestled under the eponychial fold F once fully attached, as depicted in FIG. 13. After the patient's natural nail has regrown with minimal deformity for a sufficient length of time, the sutures S will be removed to allow the splint plate 12 to be removed out from under the patient's eponychial fold F and off the top surface of the patients newly formed nail. Alternatively, the sutures S may be dissolvable after an interval of time corresponding to sufficient regrowth of the patient's nail, thereby removing the need for the patient to go to a medical professional to have the splint plate 12 removed.

The foregoing description has been presented for the purposes of illustration and description. It is not intended to be exhaustive or to limit the disclosure to the precise form disclosed. Many modifications and variations are possible in view of this disclosure. Indeed, while certain features of this disclosure have been shown, described and/or claimed, it is not intended to be limited to the details above, since it will be understood that various omissions, modifications, substitutions and changes in the apparatuses, forms, method, steps and system illustrated and, in its operation, can be made by those skilled in the art without departing in any way from the spirit of the present disclosure.

Furthermore, the foregoing description, for purposes of explanation, used specific nomenclature to provide a thorough understanding of the disclosure. However, it will be apparent to one skilled in the art that specific details are not required in order to practice the disclosure. Thus, the foregoing descriptions of specific embodiments of the present disclosure are presented for purposes of illustration and description. They are not intended to be exhaustive or to limit the disclosure to the precise forms disclosed, many modifications and variations are possible in view of the above teachings. The embodiments were chosen and described in order to best explain the principles of the disclosure and its practical applications, to thereby enable others skilled in the art to best utilize the disclosed system and method, and various embodiments with various modifications as are suited to the particular use contemplated.

The invention claimed is:

1. An adjustable nail bed splint configured to be fitted to any of a plurality of patient-specific nail beds of varying shapes, the adjustable nail bed splint comprising a splint plate having a proximal end portion and a distal end portion spaced apart along a longitudinal axis and first and second longitudinal edge margins spaced apart along a lateral axis perpendicular to the longitudinal axis, the splint plate configured to be adjusted for fitment to a patient-specific nail bed, the splint plate being stiffer along the longitudinal axis than along the lateral axis to facilitate deforming the splint plate laterally to generally conform to a lateral curvature of the patient-specific nail bed;

wherein the splint plate comprises a plurality of parallel longitudinal bending lines spaced apart along the lateral axis;

wherein the splint plate comprises longitudinal segments between the longitudinal bending lines, and wherein by comparison, along the longitudinal bending lines and along the segments between the longitudinal bending lines, the splint plate differs in at least one of thickness, density, and composition.

2. The adjustable nail bed splint of claim 1, wherein the splint plate comprises a longitudinal groove along each of the longitudinal bending lines.

3. The adjustable nail bed splint as set forth in claim 2, wherein each of the longitudinal grooves is embossed.

4. The adjustable nail bed splint of claim 2, wherein the splint plate has a bottom contact side and an opposite top side, the longitudinal grooves being formed on the opposite top side and the bottom contact side being smooth.

5. A kit for splinting nail beds, the kit comprising:

sterile packaging; and the adjustable nail bed splint of claim 1, the adjustable nail bed splint being removably received in the sterile packaging and configured to be fitted to any of a plurality of patient-specific nail beds of varying shapes.

6. The kit as set forth in claim 5, wherein the adjustable nail bed splint is not packaging foil.

7. The kit as set forth in claim 6, wherein the adjustable nail bed splint is formed entirely from biocompatible polymer.

8. The adjustable nail bed splint of claim 1, wherein the splint plate is configured to be cut to a size corresponding to the patient-specific nail bed.

9. The adjustable nail bed splint of claim 8, wherein the splint plate includes a plurality of longitudinal cut guides extending parallel to the longitudinal axis at spaced apart locations along the lateral axis, each of the longitudinal cut guides configured to guide cutting of the splint plate along a respective longitudinal cut line to adjust a width of the splint plate along the lateral axis.

10. The adjustable nail bed of claim 1, wherein the splint plate comprises biocompatible polymer.

11. The adjustable nail bed of claim 4, wherein the biocompatible polymer is one of polyester, polyethylene, polypropylene, PEEK, PAEK, PEKK, vinyl.

12. The adjustable nail bed splint of claim 1, wherein the splint plate has a central longitudinal cross-sectional plane parallel to the longitudinal axis and a central lateral cross-sectional plane perpendicular to the longitudinal axis, wherein the splint plate has a longitudinal stiffness corresponding to deformability of the splint plate in the central longitudinal cross-sectional plane and a lateral stiffness corresponding to deformability of the splint plate in the central lateral cross-sectional plane, the longitudinal stiffness being greater than the lateral stiffness.

13. The adjustable nail bed splint of claim 1, wherein the splint plate is configured to bend more easily along the longitudinal bending lines than along longitudinal segments of the splint plate between the longitudinal bend lines.

14. The adjustable nail bed splint of claim 1, wherein the longitudinal bending lines are spaced apart along the lateral axis at a lateral spacing distance in an inclusive range of from 0.5 mm to 2 mm.

15. The adjustable nail bed splint of claim 1, wherein the splint plate is configured to be deformed to a conforming shape in which the splint plate will generally conform to the lateral curvature of the patient-specific nail bed, and wherein after being deformed to the conforming shape, the splint plate is configured to substantially maintain the conforming shape when resting on a flat surface in any orientation.

16. The adjustable nail bed splint of claim 1, wherein the proximal end portion of the splint plate is configured to be inserted between an eponychial fold and the patient-specific nail bed.

17. The adjustable nail bed splint of claim 1, wherein the splint plate is configured to be secured to the nail bed by at least one suture through an eponychial fold and at least one suture through a distal tip of a finger.

18. The adjustable nail bed of claim 1, wherein the splint plate is configured to be deformed to have a compound lateral curvature.

19. The adjustable nail bed of claim 1, wherein the splint plate is prefabricated to have an initial lateral curvature and is deformable to adjust the splint plate to an adjusted lateral curvature different from the initial lateral curvature.

20. The adjustable nail bed of claim 1, wherein the splint plate is integrally formed from a single monolithic piece of material.

* * * * *